(12) United States Patent
Canfield et al.

(10) Patent No.: US 6,935,897 B2
(45) Date of Patent: Aug. 30, 2005

(54) ELECTRICAL DEVICE CONNECTOR AND METHOD THEREFOR

(75) Inventors: David L. Canfield, Lake Hughes, CA (US); Charles L. Byers, Canyon Country, CA (US); Gary D. Schnittgrund, Granada Hills, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 0 days.

(21) Appl. No.: 10/759,340

(22) Filed: Jan. 16, 2004

(65) Prior Publication Data

US 2005/0075011 A1 Apr. 7, 2005

Related U.S. Application Data

(63) Continuation-in-part of application No. 10/678,539, filed on Oct. 3, 2003, now Pat. No. 6,821,154.

(51) Int. Cl.$^7$ ........................ H01R 13/66; H01R 33/945
(52) U.S. Cl. ....................................... 439/620
(58) Field of Search ................................. 439/689, 620

(56) References Cited

U.S. PATENT DOCUMENTS

| | | | |
|---|---|---|---|
| 4,456,942 A | 6/1984 | Bronikowski | |
| 5,000,177 A | 3/1991 | Hoffmann et al. | |
| 6,164,284 A | 12/2000 | Schulman et al. | 128/899 |
| 6,185,452 B1 | 2/2001 | Schulman et al. | 604/20 |
| 6,208,894 B1 | 3/2001 | Schulman et al. | 607/2 |

*Primary Examiner*—Javaid H. Nasri
(74) *Attorney, Agent, or Firm*—Gary D. Schnittgrund

(57) ABSTRACT

A connector (1) and method of making electrical connection between an electrical conductor (7, 11) and a removable electrical device (2). The connector (7, 11) is an elastic material, such as silicone, that is both compatible with the environment and is an electrical insulator. It forces contact between the electrical device (2) and integral contacts (10, 13) in the connector (1) by virtue of its elasticity. The electrodes (4, 6) and the electrical connections are protected from the environment to avoid electrical leakage or corrosion of the electrodes (4, 6).

3 Claims, 2 Drawing Sheets

ELECTRICAL DEVICE CONNECTOR AND METHOD THEREFOR

CROSS REFERENCE TO RELATED APPLICATION

This application is a continuation-in-part of U.S. patent application Ser. No. 10/678,539 filed Oct. 3, 2003, now U.S. Pat. No. 6,821,154.

FIELD OF THE INVENTION

This invention relates to a connector for electrical devices and methods, and more particularly to connecting electrical wires to an implantable device to enable ease of connection and to minimize risk to the living tissue during and after surgery.

DETAILED DESCRIPTION OF THE PREFERRED EMBODIMENT

Figures 1, 2:
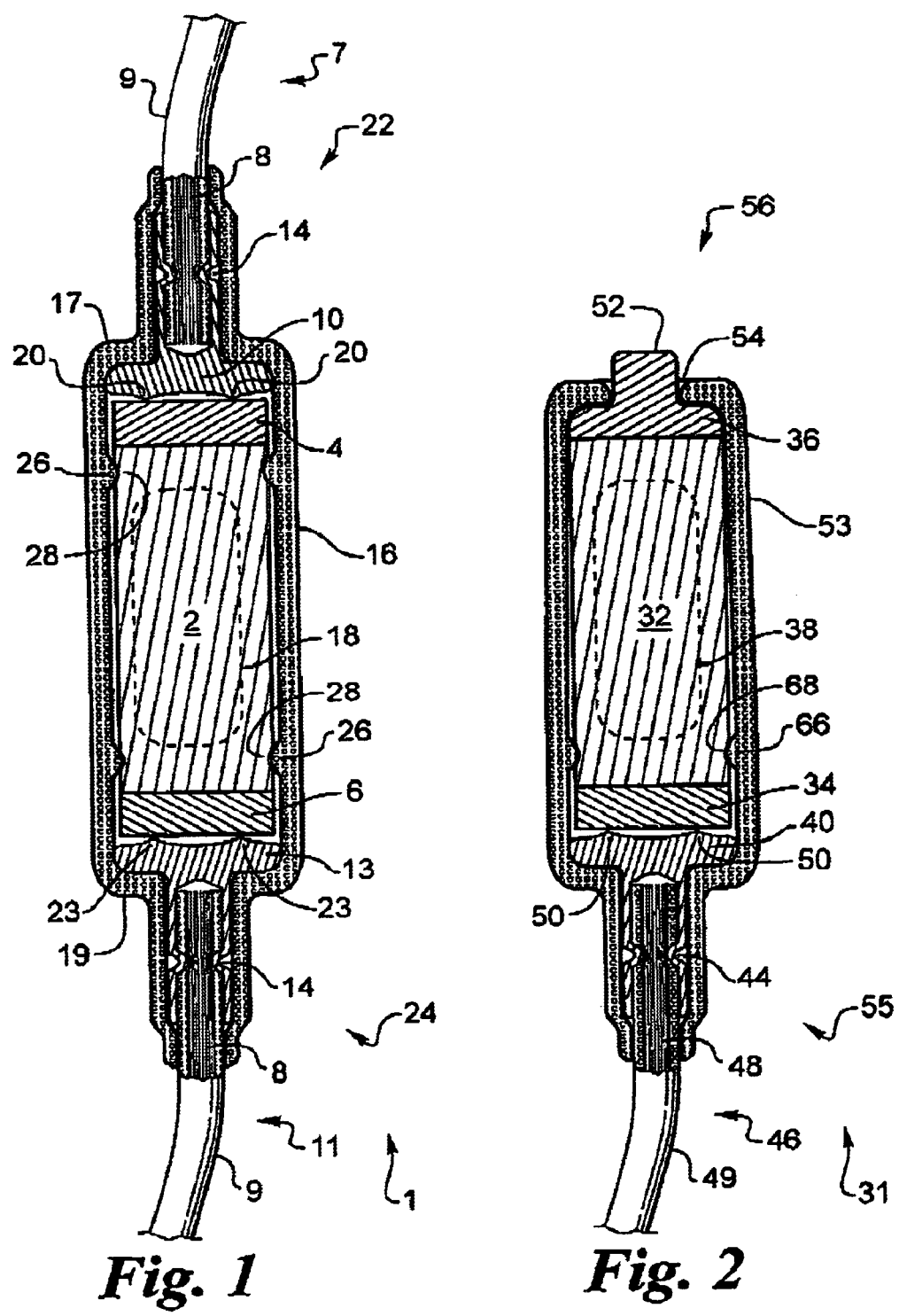
FIG. 1 illustrates a cut-away view of the connector for an implantable stimulator having a lead wire. Components are essentially figures of revolution about a central longitudinal axis.
FIG. 2 depicts a cutaway view of the connector for an implantable stimulator having a stimulating electrode extension. Components are essentially figures of revolution about a central longitudinal axis.

FIG. 1 provides a cutaway view of a preferred embodiment of a hollow boot connector 1. The connector is comprised of an elastic casing 16, preferably silicone elastomer or another material that is chosen to be compatible with the design environment. Selected silicone elastomers are biocompatible and preferred for applications involving implantation in living tissue. Silicone rubber is also known to provide enduring elastic properties in a warm saline environment. Further, the selected material is preferably an electrical insulator that minimizes leakage of electric current and that isolates the electrical device 2 from the environment.

Figure 3:
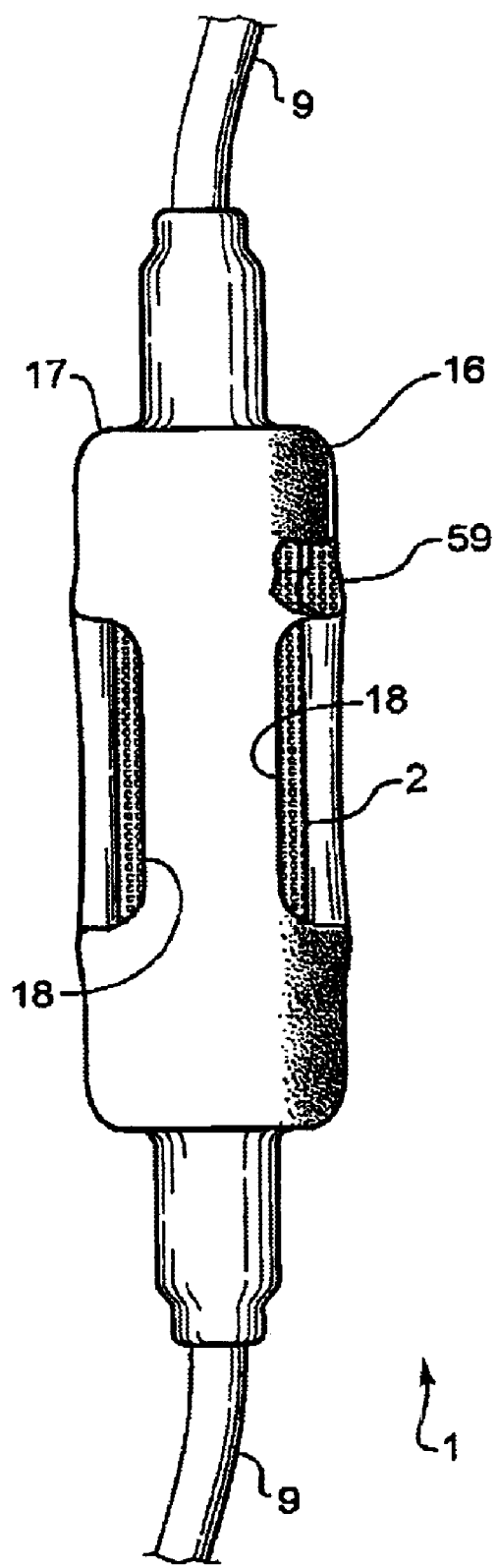
FIG. 3 depicts a view of the connector showing the increased wall thickness near the insertion opening.

The electrical casing 16, in the relaxed state, is shorter than the length of its contents. The elastic casing 16 contains at least one insertion opening 18 (dashed line) that provides access through the wall of the casing 16 and into the inside of the hollow boot connector 1, where the electrical device 2 is removably inserted. Although not evident in the figure, the edge of insertion opening 18 is shown as a single dashed line to indicate that said edge is fully rounded to reduce stress concentration. Further, as shown in FIG. 3, the wall thickness of casing 16 is progressively thickened 59 proximate the edge of insertion opening 18 in order to distribute tension stress in the edge over a larger area, and to insure that the peripheral distribution of axial compressive force is uniform, thereby eliminating any tendency to tilt the encased devices. It is known to the inventors and within the scope of the instant invention, but not illustrated herein, that a plurality of openings 18 may be present in elastic casing 16 such that there are, in essence, a plurality of bands or straps formed by the plurality of openings 18. The electrical device 2 may either be inserted before being placed into service, or during enablement for service, or as a replacement for a prior device during actual service. The connector 1 enables positive and rapid insertion of the electrical device 2 under difficult conditions, such as in seawater or in living tissue during surgery.

It is understood that the electrical device 2 encompasses electronic devices, electrical circuit components, conductors, sensors, and stimulators, such as, but not limited to devices such as the BION microstimulator of Advanced Bionics Corporation.

The hollow boot connector 1 is further comprised of at least one electrical contact 10 that is integrally connected to an electrical conductor 7, which is preferably a wire conductor 8 surrounded by a wire insulator 9. The electrical conductor 7 is preferably connected to the first electrical contact 10 by a known technique, such as crimping, as shown by crimping connection 14. Numerous embodiments rely on electrical conductor 7 to connect device 2 to a sensing or stimulating electrode comprising conductors 8 exposed at an effective location removed as desired from the location of device 2, or connected to another component or device of a system. As alternative embodiments, any of the known methods of forming a connection between a wire and a contact is applicable in lieu of crimping, as is known in the art. Preferred materials for contacts 10, 13, and 40, and for electrodes 4, 6 and 34, inexhaustibly include platinum, platinum-iridium alloys, titanium and its alloys, and stainless steel type 316L (low carbon), taken in combinations having known long-term electrochemical compatibility.

The elastic casing 16 preferably fits the electrical device 2 snugly such that when the electrical device 2 is inside the hollow boot connector 1, the first electrical contact 10 is urged toward the first electrode 4 that forms part of electrical device 2 by the stretched elastic casing 16. The first electrical contact 10 preferably has three, equally spaced nipple contacts 20 (two visible in the figure) that concentrate the contact stress between first electrical contact 10 and electrode 4, thus insuring electric continuity. In a preferred embodiment, second end 24 has second electrical contact 13 urged toward second electrode 6 by the stretched elastic casing 16, with second electrical contact 13 preferably also having three, equally spaced nipple contacts 23 that concentrate the contact stress, as described above. Preferred embodiments of contact 10 have three nipple contacts 20 in order to provide first electrical contact 10 with kinematic stability relative to electrode 4 when compressed by elastic casing 16. Further, three nipple contacts are doubly redundant, and under normal circumstances, equally share the electrical current. Nipple contacts are point-like features having a contact curvature predetermined to increase the contact stress to a value somewhat higher than the film strength of any fluid or oxide film that would otherwise intervene. Sufficient contact pressure provides a low potential drop across each contact in order to reduce or eliminate electrochemical action. Additionally, sufficient contact pressure provides a low-resistance, low-noise current path that enhances the sensitivity of a sensing device.

Illustrated in FIG. 1 is a two-conductor connector 1, having a first end 22 with a first electrical conductor 7 and a second end 24 having a second electrical conductor 11 attached to the first electrical contact 10 at the first end 22 and the second electrical contact 13 at the second end 24, respectively. In this configuration the elastic casing 16 is stretched when the electrical device 2 is inserted inside the hollow boot connector 1, which in turn urges the respective electrical contacts against the first electrode 4 and the second electrode 6.

In a preferred embodiment, the first electrical conductor 7 is integrally bonded to the elastic casing at the first end 22 to assure that there is no leakage or failure at the first end 22 which might reduce or eliminate electrical conductivity between the first electrode 4 and the first electrical contact 10. The wire insulator 9 is preferably glued to the casing 16, although it may be thermally bonded for equal effect. It will be obvious to one skilled in the art that a similar bond may be utilized at second end 24.

To insure electrical isolation between electrodes, insertion opening 18 is positioned so that it does not expose first electrode 4 or second electrode 6 of electrical device 2 to the environment surrounding the connector 1. Further, to insure electrical isolation between electrodes, at least one sealing ridge 26 may be added, in an alternative embodiment, to the inside of elastic casing 16. The sealing ridge 26 is located between insertion opening 18 and either the first electrode 4 or second electrode 6. Obviously, multiple sealing ridges may be added to facilitate an effective seal. A further embodiment adds a seal receiver 28 to electrical device 2, which mates with sealing ridge 26 to enhance the sealing effectiveness. Further, a tie (suture) (not illustrated) may be placed around the outside of the elastic casing 16 either in lieu of the sealing ridge 26 or in conjunction with it, to assure a tight seal. Obviously, sealing ridges 26 are molded in axial locations (relaxed state) predetermined to correctly position the ridges at the seal receivers 28 when the boot is stretched.

First end shoulders 17 and second end shoulder 19 of casing 16 are made somewhat thicker in order to distribute stress over a larger area during the transition from axial tension to radial tension.

Illustrated in FIG. 2 is a hollow boot connector 31 having a first end 55 and a single first conductor 46 that is comprised of a wire conductor 48 with wire insulator 49. Analogous to that described previously, the elastic casing 53 has an insertion opening 38 to accept the electrical device 32 to the interior of connector 31. When the electrical device 32 is inserted therein, the elastic casing 53 is stretched such that the electrical contact 40 and its three nipple contacts 50 (two visible in the figure) are urged into electrical contact with first electrode 34.

Analogous to the embodiment previously presented, first conductor 46 is attached to electrical contact 40 by techniques know to one skilled in the art, preferably by crimping at crimp connection 44.

In alternative embodiments, one or more sealing ridges 66 may be employed, optionally with a matching seal receiver 68 in the surface of electrical device 32 to form a tight seal. Ties, sutures, or compression bands (not illustrated) may be placed on the outside of connector 31 to facilitate the seal.

In the embodiment shown in FIG. 2, the electrical device 32 has a second electrode 36 that is further comprised of an electrode extension 52. At least a portion of electrode extension 52 protrudes from the second end 56 of connector 31 through an aperture 54 in the elastic casing 53. It is obvious that there are many electrical devices and many electrode configurations available that may be utilized with the hollow boot connector 31. The presented embodiments are not limiting, but are illustrative of connector 31 applications.

The shoulders of electrodes 10, 13, and 40 are rounded to reduce or eliminate any tendency to cut boots 16 and 53. Obviously, many modifications and variations of the present invention are possible in light of the above teachings. It is therefore to be understood that, within the scope of the appended claims, the invention may be practiced otherwise than as specifically described.

What is claimed is:

1. A hollow connector for removably mounting an electrical device having at least a first electrode, the connector comprising:

an outer elastic casing comprised of a resilient flexible material;

said connector having a first end and a second end;

a first electrical conductor extending through said first end;

the casing defining an opening, giving access to the interior of the connector, such that when the electrical device is inserted through the opening to the interior of the connector, the casing is stretched and the first electrical conductor is thereby urged against said first electrode, providing electrical communication therebetween; and said casing comprises a wall thickness that increases proximate the opening defined by said casing.

2. The hollow connector according to claim 1, wherein the casing comprises at least one shoulder.

3. The hollow connector according to claim 2, wherein the casing wall thickness increases at the shoulder.

* * * * *